United States Patent
Fan et al.

(10) Patent No.: US 10,851,317 B2
(45) Date of Patent: Dec. 1, 2020

(54) METHOD FOR PROCESSING AN INFERIOR GASOLINE AND A SYSTEM FOR PROCESSING THE SAME

(71) Applicant: China University of Petroleum-Beijing, Beijing (CN)

(72) Inventors: Yu Fan, Beijing (CN); Shihua Wang, Beijing (CN)

(73) Assignee: CHINA UNIVERSITY OF PETROLEUM-BEIJING, Beijing (CN)

( * ) Notice: Subject to any disclaimer, the term of this patent is extended or adjusted under 35 U.S.C. 154(b) by 255 days.

(21) Appl. No.: 15/881,532

(22) Filed: Jan. 26, 2018

(65) Prior Publication Data
US 2018/0312768 A1    Nov. 1, 2018

(30) Foreign Application Priority Data

Apr. 27, 2017    (CN) .......................... 2017 1 2858171

(51) Int. Cl.
*C10G 69/12*      (2006.01)
*C07C 67/00*      (2006.01)

(52) U.S. Cl.
CPC ............ *C10G 69/123* (2013.01); *C07C 67/00* (2013.01); *C10G 2300/104* (2013.01); *C10G 2300/1044* (2013.01); *C10G 2300/202* (2013.01); *C10G 2300/301* (2013.01); *C10G 2400/02* (2013.01)

(58) Field of Classification Search
CPC ............ C10G 69/123; C10G 2300/202; C10G 2400/02
See application file for complete search history.

(56) References Cited

FOREIGN PATENT DOCUMENTS

| CN | 101508912 A | 8/2009 |
|---|---|---|
| CN | 101885983 A | 11/2010 |
| CN | 102553636 A | 7/2012 |
| CN | 103666559 A | 3/2014 |
| CN | 104673377 A | 6/2015 |
| CN | 104711018 A | 6/2015 |
| CN | 104711022 A | 6/2015 |
| CN | 105255515   | 1/2016 |
| CN | 105505457 A | 4/2016 |
| CN | 107488464 A | 12/2017 |
| CN | 107488465 A | 12/2017 |

OTHER PUBLICATIONS

CN 105255515 A (English translation), Jan. 20, 2016.*
GB Application No. 1802800.1., China University of Petroleum-Beijing, Int'l Search Report dated Jul. 19, 2018.
First Office Action and Search Report dated Nov. 28, 2018 for counterpart Chinese patent application No. 2018112301856360.

* cited by examiner

*Primary Examiner* — Randy Boyer
(74) *Attorney, Agent, or Firm* — Loza & Loza, LLP; Michael F. Fedrick (57) ABSTRACT

A method for processing an inferior gasoline and a system for processing the same. In the method, a full range gasoline is subjected to a directional sulfur transfer reaction, then is cut to obtain a light gasoline fraction, a medium gasoline fraction and a heavy gasoline fraction; the light gasoline fraction is treated to obtain an alkylated light gasoline; the medium gasoline fraction is treated to obtain a raffinate oil and an extracted oil; the raffinate oil is treated to obtain an esterified medium gasoline; the heavy gasoline fraction is mixed with the extracted oil to obtain a mixed oil, and an one-stage hydrodesulfurization reaction, a two-stage hydrodesulfurization reaction, $H_2S$-removal and a hydrocarbon isomerization/aromatization reaction are carried out successively to obtain a treated heavy gasoline; blending the alkylated light gasoline, the esterified medium gasoline and the treated heavy gasoline to obtain a clean gasoline.

16 Claims, 5 Drawing Sheets

METHOD FOR PROCESSING AN INFERIOR GASOLINE AND A SYSTEM FOR PROCESSING THE SAME

CROSS-REFERENCE TO RELATED APPLICATION

This application claims priority to Chinese Patent Application No. 2017102858171, filed on Apr. 27, 2017, which is hereby incorporated by reference in its entirety.

TECHNICAL FIELD

The present disclosure relates to a method for processing an inferior gasoline and a system for processing the same.

BACKGROUND

Note that the points discussed below are not necessarily admitted to be prior art.

At present, in China, the majority (more than 70%) of the gasoline products are FCC gasolines, but China's FCC gasoline is characterized by high sulfur and high olefin. In the process of ultra-deep desulfurization and olefin reduction of FCC gasoline with high sulfur and high olefin, it certainly will cause serious loss of octane value. For the new coming National VI gasoline standard, the sulfur content is maintained ≤mg/Kg, and the olefin content is reduced to 18 v % and 15 v % in different stages, which increases the requirement of olefin reduction of FCC gasoline. This is undoubtedly a great challenge to keep the octane value of FCC gasoline.

For the production of ultra-clean high-octane gasoline, many studies have been tried to achieve desulfurization and olefin reduction of gasolines, while increasing or improving its octane value by different means. However, the development of a processing method of an inferior gasoline for ultra-deep desulfurization, olefin reduction, while maintaining or improving the octane value of gasolines is the pursuit of the researchers in this field.

SUMMARY

In one aspect, the present disclosure provides a processing method for an inferior gasoline, comprising the steps of:

allowing the inferior gasoline to be contacted with a sulfur-transfer catalyst under the condition of hydrogen and undergo a directional sulfur transfer reaction, and then cutting the gasoline to obtain a light gasoline fraction, a medium gasoline fraction and a heavy gasoline fraction;

mixing the light gasoline fraction is mixed with isobutane, wherein the olefins in the light gasoline fraction are subjected to an alkylation reaction under the action of a light gasoline alkylation catalyst to obtain an alkylated light gasoline;

obtaining an olefins-rich raffinate oil and an sulfide and aromatics-rich extracted oil by separating the medium gasoline fraction by passing through an extractive distillation system;

mixing the raffinate oil with formic acid, wherein an esterification reaction of the olefins in the raffinate oil is carried out under the action of a medium gasoline esterification catalyst, and then the unreacted formic acid is removed to obtain an esterified medium gasoline;

mixing the heavy gasoline fraction with the extracted oil to obtain a mixed gasoline, which is successively subjected to an one-stage hydrodesulfurization reaction, a two-stage hydrodesulfurization reaction and H$_2$S-removal and hydrocarbon isomerization/aromatization reaction to obtain treated heavy gasoline;

the one-stage hydrodesulfurization reaction occurs under the condition of the mixed gasoline is contacted with a one-stage selective hydrodesulfurization catalyst to remove macromolecular sulfides;

the two-stage hydrodesulfurization reaction occurs under the condition of the product of one-stage hydrodesulfurization reaction in contacted with a two-stage selective hydrodesulfurization catalyst to remove small molecular sulfides;

the hydrocarbon isomerization/aromatization reaction occurs under the condition of after the product of H$_2$S-removal is contacted with a hydrocarbon isomerization/aromatization catalyst;

re-blending the alkylated light gasoline, the esterified medium gasoline and the treated heavy gasoline to obtain a clean gasoline.

In another aspect, the present disclosure provide a processing system for an inferior gasoline which can be applied to the aforementioned processing method.

The reference numbers in the figures have the following meaning:

101: directional sulfur transfer reactor; 102: light gasoline cutting column; 103: heavy component cutting column; 104: light gasoline alkylation reactor; 105: extractive distillation system; 106: one-stage hydrodesulfurization reactor; 107: two-stage hydrodesulfurization reactor; 108: stripping column; 109: hydrocarbon isomerization/aromatization reactor; 110: medium gasoline esterification reactor; 111: coalescence dehydrator; 112: debenzolization column; 201: extractive distillation column; 202: desulfurization column; 203: regeneration column; 204: coalescence dehydrator.

DESCRIPTION OF EMBODIMENTS

The technical solutions of the present disclosure will now be described in detail in order to provide a clearer understanding of the technical features, objects and advantages of the present disclosure, but are not to be interpreted as limiting the scope of the disclosure.

In one aspect, the present disclosure provides a processing method for an inferior gasoline, comprising the steps of:

allowing the inferior gasoline to be contacted with a sulfur-transfer catalyst under the condition of hydrogen and undergo a directional sulfur transfer reaction, and then cutting the gasoline to obtain a light gasoline fraction, a medium gasoline fraction and a heavy gasoline fraction, in which the gasoline is preferable cut into the light gasoline fraction and the heavy component firstly, and then the heavy component is cut into a medium gasoline fraction and a heavy gasoline fraction;

mixing the light gasoline fraction is mixed with isobutane, wherein the olefins in the light gasoline fraction are subjected to an alkylation reaction (a light gasoline alkylation reaction) under the action of a light gasoline alkylation catalyst to obtain an alkylated light gasoline;

obtaining an olefins-rich raffinate oil and an sulfide and aromatics-rich extracted oil by separating the medium gasoline fraction by passing through an extractive distillation system;

mixing the raffinate oil with formic acid, wherein an esterification reaction (raffinate oil esterification reaction) of the olefins in the raffinate oil is carried out under the action of a medium gasoline esterification catalyst, and then the unreacted formic acid is removed to obtain an esterified medium gasoline;

mixing the heavy gasoline fraction with the extracted oil to obtain a mixed gasoline, which is successively subjected to an one-stage hydrodesulfurization reaction, a two-stage hydrodesulfurization reaction and $H_2S$-removal (It is preferable to feed the two-stage desulfurized mixed gasoline into the stripping column to separate the $H_2S$ generated during the hydrodesulfurization process) and hydrocarbon isomerization/aromatization reaction to obtain treated heavy gasoline;

the one-stage hydrodesulfurization reaction occurs under the condition of the mixed gasoline is contacted with a one-stage selective hydrodesulfurization catalyst to remove macromolecular sulfides;

the two-stage hydrodesulfurization reaction occurs under the condition of the product of one-stage hydrodesulfurization reaction in contacted with a two-stage selective hydrodesulfurization catalyst to remove small molecular sulfides;

the hydrocarbon isomerization/aromatization reaction occurs under the condition of after the product of $H_2S$-removal is contacted with a hydrocarbon isomerization/aromatization catalyst; and re-blending the alkylated light gasoline, the esterified medium gasoline and the treated heavy gasoline to obtain a clean gasoline.

This method is suitable for the modification of inferior gasoline, especially for high sulfur, high olefin catalytic cracking (fluid catalytic cracking) gasoline, which can maintain or increase the octane value of gasoline while ultra-deep desulfurization.

Preferably, the inferior gasoline is a full-range (whole fraction) FCC gasoline having a sulfur content of 300 to 2000 $\mu g \cdot g^{-1}$, and an olefin content of 25 to 50 v %.

More preferably, a sulfur content of 500 to 2000 $\mu g \cdot g^{-1}$. Such as 500, 1000, 1500, 2000 $\mu g \cdot g^{-1}$ etc.

More preferably, an olefin content of 30 to 50 v %. Such as 30%, 35%, 40%, 45%, 50% etc.

The present disclosure provides another processing method for inferior gasoline which is substantially the same as the producing method described above except that the raffinate oil is not subjected to an esterification reaction, but the raffinate oil is mixed with the product after $H_2S$ removal to carry out the hydrocarbon isomerization/aromatization reaction.

In either of the above methods, optionally, the extracted oil is subjected to a debenzolization treatment before mixing with the heavy gasoline fraction. Preferably, the debenzolization treatment is carried out when the benzene content of the full range gasoline is greater than 0.8 v %. That is, the extracted oil is subjected to debenzolization treatment first, and then mixed with the heavy gasoline fraction to obtain a mixed oil which is then subjected to the one-stage hydrodesulfurization reaction, the two-stage hydrodesulfurization reaction, $H_2S$-removal and the hydrocarbon isomerization/aromatization reaction.

As a method of a debenzolization treatment, it is possible to carry out the debenzolization treatment of the extracted oil using a debenzolization distillation system. Preferably, the debenzolization distillation system comprises a debenzolization column having a number of column plates of 20 to 50, a number of feed plates of 10 to 40; and during the debenzolization treatment, a column top temperature is controlled to be 90 to 120° C., a column top pressure to be 0.7 to 1.5 atm, a column kettle temperature to be 120 to 160° C., a column pressure to be 1.3 to 1.7 atm and a reflux ratio to be 1.5 to 2.5.

In either of the above producing methods, it is preferable that the reaction conditions of the directional sulfur transfer reaction are: a reaction pressure of 1.0 to 3.0 MPa, a liquid volume space velocity of 2.0 to 8.0 $h^{-1}$, a reaction temperature of 100 to 200° C., and a hydrogen/oil volume ratio 4 to 50.

In either of the above producing methods, it is preferable that the sulfur transfer catalyst comprises: 2 to 30 wt. % of the transition metal oxides, 0.5 to 6 wt. % of the promoters (adjuvants), 10 to 40 wt. % of the zeolites, the balance being inorganic refractory oxides, based on 100% of the total weight of the sulfur transfer catalyst; wherein the transition metal oxides may comprise one or more of NiO, CoO, ZnO, $MoO_3$, $WO_3$, CuO and the like;

The promoters may comprise a combination of one or more of $K_2O$, MgO, $La_2O_3$ and the like.

The inorganic refractory oxides may comprise a combination of one or more of alumina, silica, silicon-containing alumina and the like.

The zeolite is preferably a HZSM-5 zeolite with hierarchically pores. Preferably, the synthetic process of the HZSM-5 zeolite with hierarchically pores comprises: dissolving NaOH in deionized water at 50 to 70° C., stirring and mixing uniformly, adding $Al_2(SO_4)_3 \cdot 18H_2O$, TPABr (tetrapropylammonium bromide) and TEOS (tetraethyl orthosilicate) and mixing uniformly in order to obtain a starting sol; and the molar ratio of the raw material of the starting sol is: NaOH:TEOS=0.025 to 0.75:1, deionized water:TEOS=25 to 125:1, TPABr:$Al_2(SO_4)_3 \cdot 18H_2O$=8 to 72:1, TEOS:$Al_2(SO_4)_3 \cdot 18H_2O$=40 to 300:1; adding the polyquaternium salt PCD (the polymerization degree n=16 and the molecular weight=8000) to the above starting sol and stirring uniformly, the molar ratio of the polyquaternium salt PCD to the $Al_2(SO_4)_3 \cdot 18H_2O$ being 0.12 to 0.54:1; and then aged for 12 to 48 h, and crystallization at 150 to 180° C. for 24 to 96 h; filtered and washed, then dried at 100 to 150° C. for 8 to 24 h, to obtain the ZSM-5 zeolite with hierarchically pores composite containing template agent; the above ZSM-5 zeolite with hierarchically pores composite containing template agent is calcined at 550 to 650° C. for 4 to 8 h to remove the template agent and obtain a ZSM-5 zeolite with hierarchically pores composite without template agent; the above ZSM-5 zeolite with hierarchically pores composite is subjected to ammonium exchange treatment, 1 to 3 mol/L of $NH_4Cl$ solution can be used, the ammonium exchange treatment is performed with the mass ratio of $NH_4Cl$ solution:composite (liquid-solid) being 10:1, the treatment temperature is 50 to 100° C., and the ammonium exchange treatment is performed twice. After each ammonium exchange treatment is completed, the resulting products are dried at 100 to 150° C. for 4 to 8 h, calcined at 400 to 600° C. for 3 to 10 h, to obtain HZSM-5 zeolite with hierarchically pores composite.

In either of the above producing methods, it is preferable that the cutting temperature between the light gasoline fraction and the medium gasoline fraction is any point in the range of 30 to 60° C., and the cutting temperature between the medium gasoline fraction and the heavy gasoline fraction is higher than any point in the range of 60 to 150° C. For example, the cutting temperature between the light gasoline fraction and the medium gasoline fraction is 50° C., the cutting temperature between the medium gasoline fraction and the heavy gasoline fraction is 120° C., that is, the fraction obtained at a temperature of not more than 50° C. is the light gasoline fraction, the fraction obtained at a temperature of more than 50° C. to 120° C. is the medium gasoline fraction, the fraction obtained at a temperature of more than 120° C. is the heavy gasoline fraction.

In either of the above producing methods, it is preferable that the alkylation reaction conditions of the light gasoline are: the pressure is 2.0 to 5.0 MPa, the temperature is 60 to 150° C., the volume space velocity is 1.0 to 3.0 $h^{-1}$ based on isobutane, the molar ratio of isobutane and olefins in the light gasoline fraction is 1 to 10:1.

In either of the above producing methods, it is preferable that the specific preparation steps and compositions of the alkylation catalysts of the light gasoline are as follows:

The catalysts can be prepared according to the method described in CN102553636A (Patent No. ZL201010605454.3) (the entire disclosure of CN102553636A is incorporated herein by reference), and the composition of the alkylation catalyst is the same as that of CN102553636A.

In either of the above producing methods, it is preferable that the extractive distillation system comprises an extractive distillation column, a desulfurization column, an extraction oil dehydrator and a regeneration column, the steps of obtaining the olefin-rich raffinate oil and the sulphide- and aromatic-rich extracted oil by passing through the extractive distillation system includes:

the medium gasoline fraction enters the extractive distillation column, and being sufficiently contacted with the extraction solvent injected from the top of the extractive distillation column (extraction solvent dissolves the sulfide and the aromatics in the medium gasoline), the raffinate oil as the top product and the mixture of the extracted oil and the solvents as the bottom product are obtained by the rectification separation, a part of the raffinate oil as the top product is reflux, a part of the raffinate oil is used as the product of the step, and the mixture of the extracted oil and the solvents as the bottom product is sent into the desulfurization column for rectification;

a water vapor and a regenerated solvent from the regeneration column is introduced into the bottom of the desulfurization column, a mixture of the extracted oil and water as the top product, and the solvent as the bottom product are obtained by the rectification separation, the mixture of the extracted oil and water is layered to obtain a pre-dehydration extracted oil and water, a part of the pre-dehydration extracted oil is reflux, a part of the pre-dehydration extracted oil is dehydrated by a extraction oil dehydrator to obtain the extracted oil, the extracted oil is the product of this step, a part of the solvent obtained at the bottom is returned to the extractive distillation column being as the extraction solvent, a part of the solvent obtained is sent into the regeneration column for solvent regeneration;

a water vapor is introduced into the bottom of the regeneration column and used to strip the entering solvent to obtain water vapor and the regenerated solvent and the deactivated solvent (high boiling point cracked polycondensate), the water vapor and the regenerated solvent are discharged from the top of the regeneration column and returned to bottom of the desulfurization column, and the deactivated solvent is discharged from the bottom of the regeneration column.

In either of the above producing methods, it is preferable that the extraction solvent includes one or more of diethylene glycol, triethylene glycol, tetraethylene glycol, dimethyl sulfoxide, sulfolane, N-formyl morpholine, N-methyl-pyrrolidone, polyethylene glycol, propylene carbonate and the like.

In either of the above producing methods, it is preferable that the number of column plates of the extractive distillation column is 50 to 100, the number of feed plates is 30 to 70, the operating conditions are controlled to be: the column top temperature is 60 to 110° C., the column top pressure is 0.1 to 1 atm, the column kettle temperature is 140 to 200° C., the column kettle pressure is 0.5 to 1.5 atm, the reflux ratio is 0.1 to 3, the mass ratio of the extraction solvent to the medium gasoline fraction is 1 to 10:1.

It is preferable that the number of column plates of the desulfurization column is 15 to 35, the number of feed plates is 1 to 20, the operating conditions are controlled to be: the column top temperature is 40 to 80° C., the column top pressure is −1 to 0 atm, the column kettle temperature is 140 to 200° C., the column kettle pressure is −1 to 0 atm, the reflux ratio is 0.1 to 3.

It is preferable that the extraction oil dehydrator is a coalescence dehydrator.

It is preferable that the column top temperature of the regeneration column is controlled to 100 to 200° C., the mass ratio of the introduced water vapor to the entering solvent is 0.5 to 5:1.

It is more preferable that satisfying one or more of the above preferred embodiments at the same time (for example, all) to obtain the raffinate oil and the extracted oil.

In either of the above producing methods, it is preferable that the step of "the olefin in the raffinate oil is subjected to an esterification reaction, and then the unreacted formic acid is removed to obtain an esterified medium gasoline" comprising the following steps:

mixing the raffinate oil with formic acid, and adding the mixture into the medium gasoline esterification reactor, and by contacting with a medium gasoline esterification catalyst, the olefins in the raffinate oil is esterified to obtain an esterified product;

removing the formic acid in the esterified product by an extraction operation and then the resultant being dehydrated to obtain an esterified medium gasoline; it is preferable that the esterified product is mixed with the formic acid extractant—water and/or formic acid aqueous solution (water in the formic acid extractant extract the unreacted formic acid in the esterified product), and the mixture is stirred and layered to obtain an aqueous esterified medium gasoline and formic acid aqueous solution extract, after dehydration of the aqueous esterified medium gasoline, the esterified medium gasoline is obtained.

According to the actual situation, a part of the resulting formic acid aqueous solution extract can be separated and purified, and the other part can be used directly as the formic acid extractant or as formic acid extractant after being mixed with water. It is preferable that the mass ratio of the formic acid aqueous solution extract being to separate and purify and being as the formic acid extractant is 1:20 to 200.

In either of the above producing methods, it is preferable that the esterification reaction conditions of the raffinate oil are: the reaction temperature is 80 to 200° C., the reaction pressure is 0.1 to 6.0 MPa, the weight ratio of the formic acid to the olefin in the raffinate oil (acid/olefin ratio) is 0.5 to 2.5:1.0, the liquid volume space velocity is 0.5 to 5.0 $h^{-1}$ basing on formic acid.

It is preferable that the aqueous esterified medium gasoline is dehydrated by a coalescence dehydrator.

In either of the above producing methods, it is preferable that the medium gasoline esterification catalyst is the esterification catalyst having a high secondary ester selectivity, including a combination of one or more of a metal oxide catalyst, a zeolite molecular sieve catalyst, a $SO_4^{2-}/M_xO_y$ catalyst, a strong acid cation exchange resin catalyst, and the like; in $M_xO_y$, x is 1 to 5, y is 1 to 8.

It is preferable that the metal oxide catalyst comprises a catalyst made of at least one of silica, molecular sieve and diatomite, and the like as a carrier loading at least one metal oxide such as ZnO, SnO and $Al_2O_3$, and the like. The carrier may have a microporous structure or a mesoporous structure.

It is preferable that the zeolite molecular sieve catalyst comprises the molecular sieve catalyst mixed of one or more an aluminum phosphate molecular sieve, a silicoaluminophosphate molecular sieve, a H-type mordenite, a HY zeolite, a H-β zeolite, a HZSM-5 zeolite and silicon-containing alumina, and the like. The zeolite molecular sieve may be zeolite with micropores molecular sieve or zeolite with hierarchically pores molecular sieve.

It is preferable that the $SO_4^{2-}/M_xO_y$ catalyst may include a $SO_4^{2-}/M_xO_y$ catalyst prepared by loading $SO_4^{2-}$ onto a carrier made of at least one metal oxide such as ZrO, ZnO, SnO and the like.

It is preferable that the strong acid cation exchange resin catalyst includes a mesoporous-macroporous high molecular cross-linked polymer catalyst comprising a strong acid reactive group. For example, the strong acid reactive group is sulfonic acid group-$SO_3H$, and the like.

In either of the above producing methods, the mixed oil obtained by mixing the heavy gasoline fraction and the extracted oil contacts in succession with an one-stage selective hydrodesulfurization catalyst and a two-stage selective hydrodesulfurization catalyst to undergo the one-stage hydrodesulfurization reaction and the two-stage hydrodesulfurization reaction respectively, and the one-stage hydrodesulfurization reactor and the two-stage hydrodesulfurization reactor are arranged in series; and then the resultant enters the stripping column, and $H_2S$ is separated; and then the resulting material contacts with a hydrocarbon isomerization/aromatization catalyst to undergo a hydrocarbon isomerization/aromatization reactions.

It is preferable that the conditions of the one-stage hydrodesulfurization reaction are: the reaction pressure is 1.0 to 3.0 MPa, the liquid volume space velocity is 3.0 to 6.0 $h^{-1}$, the reaction temperature is 200 to 300° C., and the hydrogen/oil volume ratio is 200 to 600.

It is preferable that the conditions of the two-stage hydrodesulfurization reaction are: the reaction pressure is 1.0 to 3.0 MPa, the liquid volume space velocity is 3.0 to 6.0 $h^{-1}$, the reaction temperature is 300 to 400° C., and the hydrogen/oil volume ratio is 200 to 600.

It is preferable that the bottom temperature of the stripping column is controlled to be 150 to 200° C., the column top temperature is 60 to 120° C., and the pressure is 0.1 to 2 MPa.

It is preferable that the reaction conditions of the hydrocarbon isomerization/aromatization reaction are: the reaction pressure is 1.0 to 3.0 MPa, the liquid volume space velocity is 1.0 to 4.0 $h^{-1}$, the reaction temperature is 340 to 430° C., and the hydrogen/oil volume ratio is 200 to 600.

It is more preferable that one or more (e.g., all) of the above preferable conditions are satisfied at the same time to obtain the treated heavy gasoline.

The selectivity in the one-stage selective hydrodesulfurization catalyst or the two-stage selective hydrodesulfurization catalyst of the present disclosure is to select a hydrodesulfurization reaction between hydrodesulfurization and olefin saturation.

In either of the above producing methods, it is preferable that the one-stage selective hydrodesulfurization catalyst comprises: $MoO_3$ 10 to 18 wt. %, CoO 2 to 6 wt. %, $K_2O$ 1 to 7 wt. %, $P_2O_5$ 2 to 6 wt. %, and the balance being Al—Si—Mg composite oxide carrier based on 100% of the total weight of the one-stage selective hydrodesulfurization catalyst, and the weight composition of the Al—Si—Mg composite oxide in the catalyst is: $Al_2O_3$ 60 to 75 wt. %, $SiO_2$ 5 to 15 wt. % and MgO 3 to 10 wt. %.

In either of the above producing methods, it is preferable that the two-stage selective hydrodesulfurization catalyst comprises: $MoO_3$ 3 to 10 wt. %, NiO 5 to 20 wt. %, $K_2O$ 1 to 7 wt. % and the balance being Al—Si composite oxide carrier based on 100% of the total weight of the two-stage selective hydrodesulfurization catalyst, and the weight composition of the Al—Si composite oxide in the catalyst is: $Al_2O_3$ 60 to 75 wt. %, $SiO_2$ 5 to 15 wt. %.

In either of the above producing methods, it is preferable that the hydrocarbon isomerization/aromatization catalyst comprises: $MoO_3$ 4 to 8 wt. %, CoO 1 to 4 wt. %, $P_2O_5$ 1 to 3 wt. %, modified HZSM-5 zeolite 50 to 70 wt. % and the balance being Al—Ti composite oxide binder based on 100% of the total weight of hydrocarbon isomerization/aromatization catalyst; and the weight composition of the Al—Ti composite oxide binder in the catalyst is: $Al_2O_3$ 70 to 95 wt. %, $TiO_2$ 5 to 30 wt. %; the modified HZSM-5 zeolite is a product of HZSM-5 zeolite treated by hydrothermal treatment and modified treatment of mixed acid solution of inorganic acids and organic acids.

It is preferable that either of the above producing method further comprises drying and pre-sulfurization of the directional sulfur transfer catalyst, the one-stage selective hydrodesulfurization catalyst, the two-stage selective hydrodesulfurization catalyst and the hydrocarbon isomerization/aromatization catalyst respectively before an reaction.

It is preferable that the drying conditions are: at 100 to 150° C., under $N_2$ atmosphere, with the $N_2$ space velocity being 200 to 2000 $h^{-1}$.

It is preferable that the pre-sulfurization steps are: completely replacing $N_2$ in the catalyst bed by $H_2$ and maintaining the space velocity of $H_2$ being 500 to 3000 $h^{-1}$, adjusting the temperature of the catalyst bed to 120 to 180° C., adding a straight-run naphtha to the catalyst bed in a volume space velocity of 1 to 5 $h^{-1}$, adjusting the hydrogen/oil volume ratio to 200 to 500:1; the catalyst bed is heated to 150 to 200° C. at a speed of 10 to 30° C./h, beginning to inject the vulcanizing agent (e.g., dimethyl disulfide), adjusting the injection rate to 1 to 5 wt. % of that of the straight-run naphtha; and continuing to heat to 210 to 250° C. at a speed of 10 to 30° C./h, and keeping the temperature for 6 to 10 h; heating to 270 to 290° C. at a speed of 10 to 30° C./h, and keeping the temperature for 6 to 10 h; heating to 310 to 350° C. at a speed of 10 to 30° C./h, and keeping the temperature for 6 to 10 h; cooling the reaction temperature of each catalyst bed at a speed of 10 to 30° C./h; finally, the vulcanized oil in the system is replaced by an oil for reaction, and the vulcanization is ended.

In another aspect, the present disclosure provides a processing system for an inferior gasoline which can be applied to the aforementioned producing method, the processing system comprises a directional sulfur transfer reactor, a light gasoline cutting column used for cutting in order to obtain the light gasoline fraction and the heavy components, a heavy component cutting column used for cutting in order to obtain the medium gasoline fraction and the heavy gasoline fraction, a light gasoline alkylation reactor, an extractive distillation system used for separate the extracted oil and the raffinate oil, a medium gasoline esterification reactor, a formic acid extraction system, a medium gasoline dehydrator, an one-stage hydrodesulfurization reactor, a two-stage hydrodesulfurization reactor, a stripping column, and a hydrocarbon isomerization/aromatization reactor;

Wherein the directional sulfur transfer reactor is provided with a feed inlet, a reactant outlet of the directional sulfur transfer reactor is connected with the feed inlet of the light gasoline cutting column through a pipeline, the light gasoline fraction outlet of the light gasoline cutting column is connected with the inlet of raw material of reaction of the light gasoline alkylation reactor through a pipeline, the heavy component outlet of the light gasoline cutting column is connected with the feed inlet of the heavy component cutting column through a pipeline, the medium gasoline fraction outlet of the heavy component cutting column is connected with the extractive distillation system through a pipeline, the raffinate oil outlet of the extractive distillation system is connected with the inlet of raw material of reaction of the medium gasoline esterification reactor through a pipeline, the reactant outlet of the medium gasoline esterification reactor is connected with the formic acid extraction system through a pipeline, the outlet of the formic acid extraction system is connected with the feed inlet the medium gasoline dehydrator through a pipeline, the heavy gasoline fraction outlet of the heavy component cutting column is connected with the feed inlet of the one-stage hydrodesulfurization reactor through a pipeline, the extracted oil outlet of the extractive distillation system is connected with the feed inlet of the one-stage hydrodesulfurization reactor through a pipeline, the one-stage hydrodesulfurization reactor, the two-stage hydrodesulfurization reactor, the stripping column and the hydrocarbon isomerization/aromatization reactor arrange in series with each other; the alkylated light gasoline outlet of the light gasoline alkylation reactor, the esterified medium gasoline outlet of the medium gasoline dehydrator and the treated heavy gasoline outlet of the hydrocarbon isomerization/aromatization reactor are each connected to a storage tank.

Alternatively, the raffinate oil outlet of the extractive distillation system is not connected with the inlet of raw material of reaction of the medium gasoline esterification reactor, but is directly connected with the inlet of raw material of reaction of the hydrocarbon isomerization/aromatization reactor through a pipeline. In the aforementioned processing system, the alternative system is without a medium gasoline esterification reactor, a formic acid extraction system and a medium gasoline dehydrator. Instead, the raffinate oil outlet of the extractive distillation system is directly connected with the inlet of raw material of reaction of the hydrocarbon isomerization/aromatization reactor through a pipeline, and the rest is the same as the aforementioned processing system.

Optionally, in any of the above processing system, a debenzolization column is provided on the pipeline between the extracted oil outlet of the extractive distillation system and the reaction feed inlet of the one-stage hydrodesulfurization reactor, the debenzolized and extracted oil outlet of the debenzolization column is connected with the one-stage hydrodesulfurization reactor.

In any of the above producing system, it is preferable that the medium gasoline dehydrator is a coalescence dehydrator.

In any of the above producing system, it is preferable that the extractive distillation system comprises an extractive distillation column, a desulfurization column, an extraction oil dehydrator and a regeneration column, on the top of the extractive distillation column is provided with an extraction solvent inlet, the feed inlet of the extractive distillation column is connected with the medium gasoline fraction outlet through a pipeline, the top of the extractive distillation column is provided with a raffinate oil outlet equipped with a reflux device, the bottom product outlet of the extractive distillation column is connected with the feed inlet of the desulfurization column through a pipeline, on the top of the desulfurization column is provided with a pre-dehydration extracted oil outlet and a reflux inlet equipped with a reflux device, the extraction oil dehydrator is provided with a pre-dehydration extracted oil inlet and a extracted oil outlet, the pre-dehydration extracted oil outlet on the top of the desulfurization column is connected with a reflux inlet on the top of the desulfurization column and a pre-dehydration extracted oil inlet of the extraction oil dehydrator respectively, the kettle of the desulfurization column is provided with a water vapor and solvent inlet, the bottom product outlet of the desulfurization column is connected with the extraction solvent inlet and the feed inlet of the regeneration column through a pipeline respectively, the kettle of the regeneration column is provided with a water vapor inlet, the top product outlet of the regeneration column is connected with the water vapor and the solvent inlet of the desulfurization column through a pipeline, the regeneration column is provided with a deactivated solvent outlet.

It is preferable that the extraction oil dehydrator is a coalescence dehydrator.

It is more preferable that any of the aforementioned system employs one or more (e.g., all) of the above preferred embodiments.

In summary, the present disclosure provides a processing method and a processing system for an inferior gasoline, which is particularly suitable for high sulfur and high olefin fluid catalytic cracking gasoline, and is capable of ultra-deep desulfurization while maintaining or improving the octane value of gasolines. Compared with the prior art, in the present disclosure, the light gasoline fraction is mixed with isobutane, an alkylation reaction is occurred between the olefins in the light gasoline fraction and isobutane to produce multi-branched isoparaffins with high octane value, which improves the octane value of the light gasoline; performing a extractive distillation of the medium gasoline fraction to obtain an olefin-rich raffinate oil and a sulphide- and aromatics-rich extracted oil, the raffinate oil is mixed with formic acid and the olefin in the raffinate oil undergoes an esterification reaction with formic acid to produce esters with high octane value, or directly undergoes an isomerization/aromatization reaction to produce aromatics and multi-branched hydrocarbons with high octane value, the octane value of the medium gasoline is further improved; For the inferior gasoline with too high benzene content, benzene is mainly concentrated in the extracted oil in the medium gasoline fraction, the debenzolization treatment of the extracted oil makes the final blended gasoline product to meet the requirements of the National VI standard for the benzene content; a two-stage hydrodesulfurization is performed on the heavy gasoline fraction, the removal of large molecules of sulfur is performed firstly, and then remove the small molecules of sulfur (sulfides such as thiols produced by olefins and $H_2S$ generated by one-stage hydrodesulfurization), $H_2S$ is separated, and then the next step of the hydrocarbon isomerization/aromatization reaction is performed, avoiding $H_2S$ produced by hydrodesulfurization and olefins continue to produce thiols. The producing method provided by the present disclosure upgrading a inferior gasoline with a sulfur content of 300 to 2000 $\mu g \cdot g^{-1}$, an olefin content of 25 to 50 v % to a high quality National VI gasoline product with a sulfur content ≤10 $\mu g \cdot g^{-1}$, an olefin content ≤15 v %, and the method makes the octane value being without lost or being improved.

Example 1

The Example provides a method for processing an inferior gasoline, which uses the FCC gasoline (full range gasoline, raw oil 1) with a sulfur content of 625.3 $\mu g \cdot g^{-1}$, a olefin content of 35.6 v %, a aromatics content of 14.4 v %, a isoparaffin content of 18.2 v %, a benzene content of 0.7 v % as the raw material, wherein the composition ratio of each catalyst is as follows, based on the total weight of each catalyst:

Directional sulfur transfer catalyst: 12 wt. % NiO, 6 wt. % $MoO_3$, 2 wt. % $La_2O_3$, 20 wt. % HZSM-5 with hierarchically pores, 60 wt. % $Al_2O_3$—$SiO_2$ (silicon-containing alumina);

Light gasoline alkylation catalyst: 60 wt. % modified β-zeolite, 10 wt. % HY zeolite, 8 wt. % kaolin (containing 19 wt. % $Al_2O_3$, 3 wt. % $P_2O_5$);

Medium gasoline esterification catalyst: 50 wt. % HZSM-5, 50 wt. % $Al_2O_3$—$SiO_2$ (silicon-containing alumina);

Medium gasoline extraction solvent: 90 wt. % sulfolane and 10 wt. % tetraethylene glycol;

One-stage selective hydrodesulfurization catalyst: 4 wt. % CoO, 12 wt. % $MoO_3$, 3 wt. % $K_2O$, 2 wt. % $P_2O_5$ and Al—Si—Mg composite oxides, the Al—Si—Mg composite oxide is consisting of 67 wt. % $Al_2O_3$, 8 wt. % $SiO_2$, 4 wt. % MgO;

Two-stage selective hydrodesulfurization catalyst: 8.0 wt. % NiO, 5.4 wt. % $MoO_3$, 1.2 wt. % $K_2O$ and Al—Si composite oxide carrier, the Al—Si composite oxide carrier is consisting of 76.3 wt. % $Al_2O_3$, 9.1 wt. % $SiO_2$; and Hydrocarbon isomerization/aromatization catalyst: 2.0 wt. % CoO, 6.0 wt. % $MoO_3$, 1.0 wt. % $P_2O_5$, 65.0 wt. % HZSM-5 and Al—Ti composite oxide binder, the Al—Ti composite oxide binder is consisting of 21.0 wt. % $Al_2O_3$, 5.0 wt. % $TiO_2$.

The specific preparation steps of the directional sulfur transfer catalyst are as follows: 2.12 g NaOH and 280 mL deionized water were stirred and mixed at 60° C., 1.4 g $Al_2(SO_4)_3 \cdot 18H_2O$, 10.48 g TPABr and 26.16 g TEOS were added and mixed uniformly in order to obtain the mixed system of the starting sol; adding 5.4 g polyquaternium PCD (polymerization degree n=16, molecular weight of 8000) to the mixed system of the starting sol, aged for 24 h after the mixed system is stirred uniformly; the resulting final mixture was transferred to a stainless steel reaction kettle with a polytetrafluoroethylene liner, crystallizing at 170° C. for 72 h; the crystallized product was ultrasonically cleaned and separated in order to obtain the ZSM-5 zeolite with hierarchically pores composite containing template agents, which was washed with deionized water to pH=7 to 8, and then dried at 120° C. for 12 h to obtain a ZSM-5 zeolite with hierarchically pores composite containing template agents; calcining the above HZSM-5 zeolite with hierarchically pores composite containing template agents at 600° C. for 6 h in order to remove the template agent, to obtain a HZSM-5 zeolite with hierarchically pores composite without template agents; the above ZSM-5 zeolite with hierarchically pores composite is subjected to ammonium exchange treatment using 2 mol/L $NH_4Cl$ solution, the ammonium exchange treatment is performed in a liquid:solid (NH4Cl solution: composite) mass ratio of 10:1, the treatment temperature is 80° C., and the ammonium exchange treatment is performed twice, after each ammonium exchange treatment is completed, the obtained products were dried at 120° C. for 6 h, calcined at 500° C. for 4 h to obtain HZSM-5 zeolite with hierarchically pores composite.

60.0 g of Si—Al powder (containing $Al_2O_3$ 92.0 wt. %, SiO 8.0 wt. %), 20.0 g of the above HZSM-5 with hierarchically pores and 2.5 g of sesbania powder were weighted, ground and homogenized, to which 6 ml of 65 wt. % nitric acid aqueous solution was added, fully kneaded, molded by an extruder, dried at 120° C. for 4 h, and calcined at 550° C. for 5 h, then a cloverleaf pattern catalyst carrier with a diameter of 2 mm was obtained;

Nickel nitrate, ammonium molybdate and lanthanum nitrate mixed solution were prepared based on the stoichiometric ratio. Then, the immersion liquid was uniformly added to the above catalyst carrier by equal volume impregnation method and dried at 120° C. for 4 h, calcined at 550° C. for 4 h, then a directional sulfur transfer catalyst was obtained.

The specific preparation steps of the alkylation catalyst are as follows:

It can be prepared according to the method described in Example 7 in CN102553636A (Patent No. ZL201010605454.3) (Example 7 of CN102553636A is incorporated herein by reference).

The specific preparation steps of the medium gasoline esterification catalyst are as follows:

ZSM-5 zeolite with a Si/Al ratio of 35 and 1 mol/L $NH_4Cl$ aqueous solution was mixed at a weight ratio of 1:10, stirred at 80° C. for 4 h, filtered, washed, dried and calcined at 550° C. for 5 h; the above process was repeated once to obtain ammonium exchanged HZSM-5 zeolite.

30.0 g of Si—Al powder (containing $Al_2O_3$ 92.0 wt. %, SiO 8.0 wt. %), 20.0 g of the above HZSM-5 zeolite and 1.9 g of sesbania powder were weighted, ground and homogenized, to which 4.5 ml of 65 wt. % nitric acid aqueous solution was added, fully kneaded, molded by an extruder, dried at 120° C. for 4 h, and calcined at 550° C. for 5 h, then a cloverleaf pattern light gasoline esterification catalyst with a diameter of 2 mm was obtained.

The specific preparation steps of the one-stage selective hydrodesulfurization catalyst are as follows:

70.0 g of a Al—Si—Mg composite powder with proper Al/Si/Mg ratio (water content of 25 wt. %) and 2.0 g of sesbania powder were weighted, ground and homogenized, to which 5 mL of nitric acid aqueous solution with a mass concentration of 65 wt. % was added, after fully kneaded, a cloverleaf pattern bar with a diameter of 2 mm was extruded from an extruder, and was dried at 120° C. for 3 h, and calcined at 520° C. for 4 h, then a molded catalyst carrier was obtained; 40.0 g of the above catalyst carrier was immersed in a mixed impregnation solution of 35 mL of potassium nitrate and diammonium phosphate, and the impregnation solution contains 1.5 g of $K_2O$ and 1.0 g of $P_2O_5$, based on the oxides, and then aged for 5 h at room temperature, and further dried at 120° C. for 3 h, calcined at 520° C. for 4 h, a catalyst carrier loading potassium and phosphorus was obtained; 32.0 mL of a cobalt nitrate and ammonium molybdate mixture solution containing 2.0 g of CoO and 6.1 g of $MoO_3$ (the content of each active ingredient is based on the oxide form, which does not limit the active ingredient in the mixture is present as an oxide) was formulated, and 3.0 mL of ammonia solution in water at a concentration of 17% was added and sufficiently shaken until the solid was completely dissolved to form an impregnation solution. Then, the catalyst carrier loading potassium and phosphorus was immersed in the immersion solution and aged for 5 h at room temperature, and dried at 120° C. for 3 h, calcined at 520° C. for 5 h, then a one-stage selective hydrodesulfurization catalyst was obtained.

The specific preparation steps of the two-stage selective hydrodesulfurization catalyst are as follows:

70.0 g of a Al—Si composite powder with proper Al/Si ratio (water content of 25 wt. %) and 2.0 g of sesbania powder were weighted, ground and homogenized, and 5 mL of nitric acid aqueous solution with a mass concentration of 65 wt. % was added, fully kneaded, then a cloverleaf pattern bar with a diameter of 2 mm was extruded by an extruder, which was dried at 120° C. for 3 h, and calcined at 520° C. for 4 h, a molded catalyst carrier was obtained; 40.54 g of the above catalyst carrier was immersed in an impregnation solution of 35 mL of potassium nitrate, and the impregnation solution contains 0.57 g of $K_2O$, based on the oxides, and then aged for 5 h at room temperature, and further dried at 120° C. for 3 h, calcined at 520° C. for 4 h, a catalyst carrier loading potassium was obtained; 32.0 mL of a cobalt nitrate and ammonium molybdate mixture solution containing 3.8 g NiO and 2.56 g $MoO_3$ (the content of each active ingredient is based in the form of an oxide, which does not limit the active ingredient in the mixture to be presented as an oxide) was formulated, and 3.0 mL of ammonia in water at a concentration of 17% was added and sufficiently shaken until the solid was completely dissolved to form an impregnation solution. Then, the catalyst carrier loading potassium was immersed in the immersion solution and aged for 5 h at room temperature, and dried at 120° C. for 3 h, calcined at 520° C. for 5 h, a two-stage selective hydrodesulfurization catalyst was obtained.

The specific preparation steps of the hydrocarbon isomerization/aromatization catalyst are as follows:

It can be prepared by the method described in CN101508912A (Patent No. ZL200910080112.1) (the preparation method of the two-stage catalyst in Example 1 of CN101508912A is hereby incorporated by reference), except that the inorganic acid-organic acid treatment after hydrothermal treatment in the preparation method disclosed in CN101508912A is changed to a single inorganic acid treatment after hydrothermal treatment (treatment conditions are the same).

Figure 1:
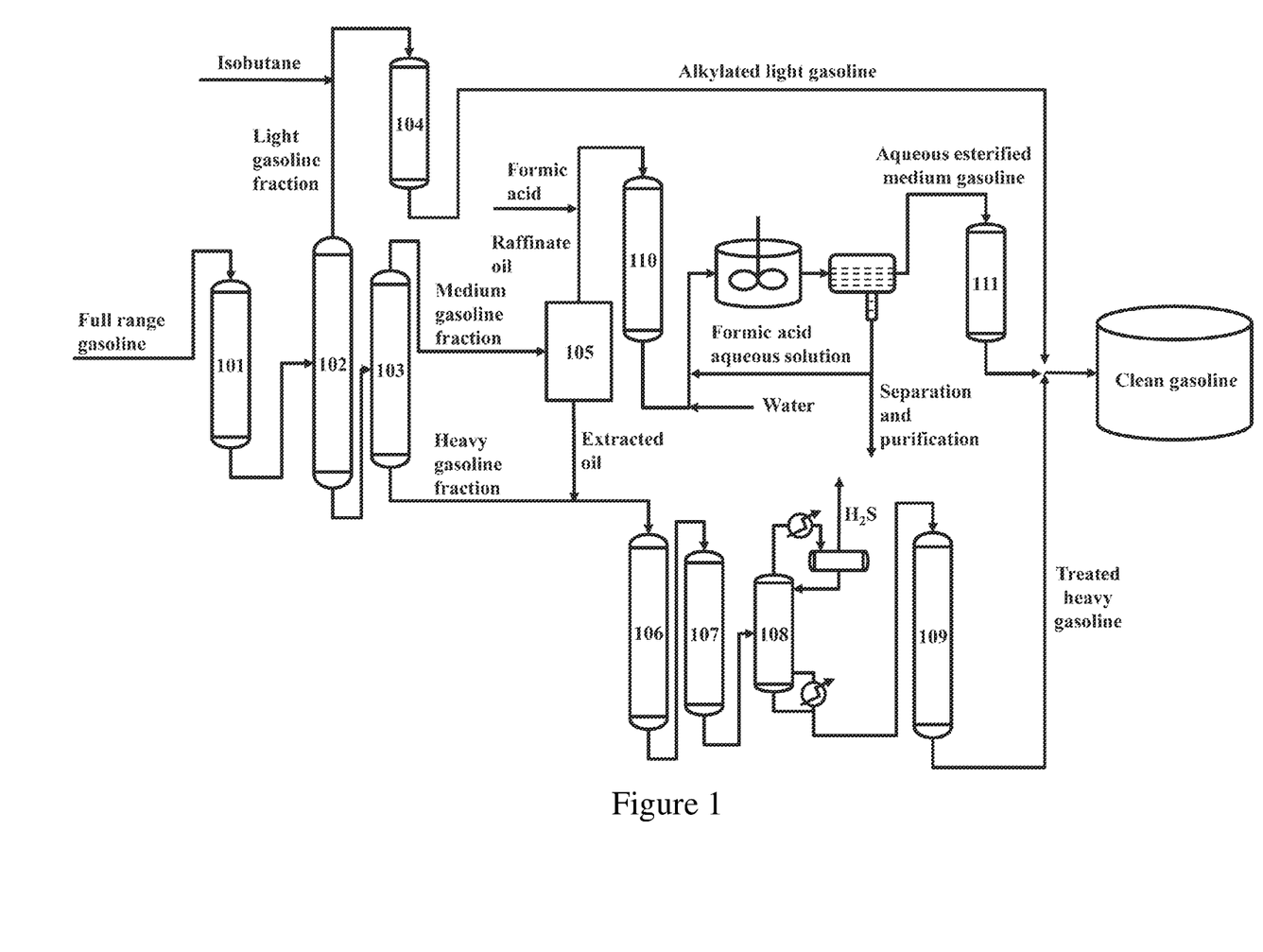
FIG. 1 is a schematic flow diagram and a system of an efficient processing method for an inferior gasoline provided in Example 1 of the present disclosure.

As shown in FIG. 1, the system comprises the directional sulfur transfer reactor 101, the light gasoline cutting column 102 used for cutting the light gasoline fraction and the heavy component, the heavy component cutting column 103 used for cutting the medium gasoline fraction and the heavy gasoline fraction, the light gasoline alkylation reactor 104, the extractive distillation system 105 for separating the extracted oil and the raffinate oil, the medium gasoline esterification reactor 110, the formic acid extraction system, the coalescence dehydrator 111, the one-stage hydrodesulfurization reactor 106, the two-stage hydrodesulfurization reactor 107, the stripping column 108, the hydrocarbon isomerization/aromatization reactor 109;

Wherein the directional sulfur transfer reactor 101 is provided with a feed inlet, the reactant outlet of the directional sulfur transfer reactor 101 is connected with the feed inlet of the light gasoline cutting column 102 through a pipeline, the light gasoline fraction outlet of the light gasoline cutting column 102 is connected with the inlet of raw material of reaction of the light gasoline alkylation reactor 104 through a pipeline, the heavy component outlet of the light gasoline cutting column 102 is connected with the feed inlet of the heavy component cutting column 103 through a pipeline, the medium gasoline fraction outlet of the heavy component cutting column 103 is connected with the extractive distillation system 105 through a pipeline, the raffinate oil outlet of the extractive distillation system 105 is connected with the inlet of raw material of reaction of the medium gasoline esterification reactor 110 through a pipeline, the reactant outlet of the medium gasoline esterification reactor 110 is connected with the formic acid extraction system through a pipeline, the outlet of the formic acid extraction system is connected with the feed inlet of the coalescence dehydrator 111 through a pipeline, the heavy gasoline fraction outlet of the heavy component cutting column 103 is connected with the feed inlet of the one-stage hydrodesulfurization reactor 106 through a pipeline, the extracted oil outlet of the extractive distillation system 105 is connected with the feed inlet of the one-stage hydrodesulfurization reactor 106 through a pipeline, the one-stage hydrodesulfurization reactor 106, the two-stage hydrodesulfurization reactor 107, the stripping column 108 and the hydrocarbon isomerization/aromatization reactor 109 are arranged in series; the alkylated light gasoline outlet of the light gasoline alkylation reactor 104, the esterified medium gasoline outlet of the coalescence dehydrator 111 and the treated heavy gasoline outlet of the hydrocarbon isomerization/aromatization reactor 109 are all connected to one storage tank.

As shown in FIG. 1, a low-temperature directional sulfur transfer reaction is occurred upon contact of the full range gasoline (i.e., raw oil 1) with a directional sulfur transfer catalyst under the condition of hydrogen in the directional sulfur transfer reactor 101. The properties of the raw oil 1 are shown in Table 1. The reaction conditions of the directional sulfur transfer reaction are: the pressure is 2.4 MPa, the temperature is 135° C., the liquid volume space velocity is 3 $h^{-1}$, the hydrogen/oil volume ratio is 7; and then, after the directional sulfur transfer reaction, the oil is subjected to light gasoline cutting in the light gasoline cutting column 102, the light gasoline fraction and the heavy component are obtained, the obtained heavy component is cut in the heavy component cutting column 103, to obtain the medium gasoline fraction and the heavy gasoline fraction. Wherein the cutting temperature of the light gasoline fraction is 65° C., the cutting temperature of the medium and heavy gasoline fraction is 120° C. That is, the fraction collected below 65° C. is the light gasoline fraction, the fraction collected between 65° C. and 120° C. is the medium gasoline fraction, the fraction collected higher than 120° C. is the heavy gasoline fraction.

The obtained light gasoline fraction is mixed with isobutane, an alkylation reaction is occurred between the olefins in the light gasoline fraction and isobutane in the alkylation reactor 104 under the action of an alkylation catalyst to obtain an alkylated light gasoline, the conditions of the reaction are: the pressure is 4.0 MPa, the temperature is 90° C., the volume space velocity is 2.0 h$^{-1}$ (based on isobutane), the molar ratio of isobutane and the olefins in the light gasoline fraction is 1.4:1.

Figure 5:
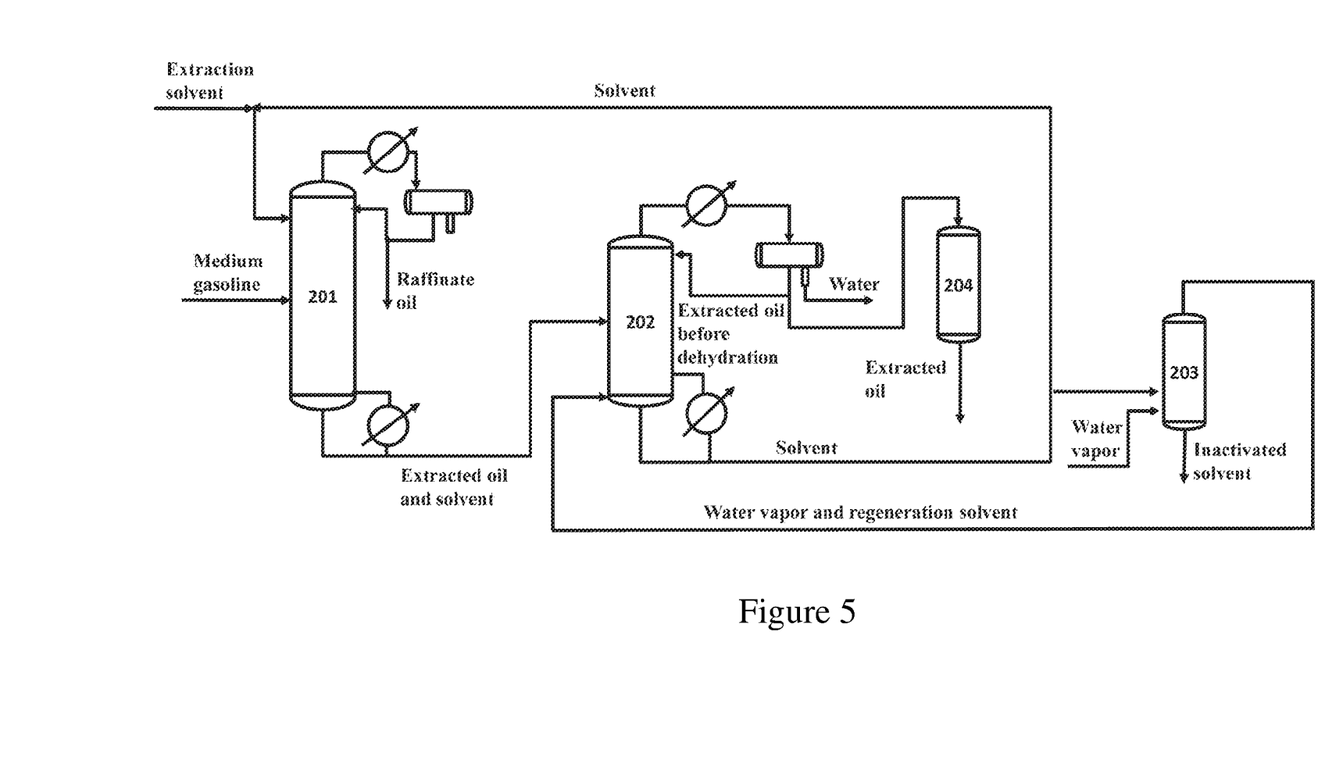
FIG. 5 is a schematic flow diagram and a system of the extractive distillation system of an efficient processing method for an inferior gasoline provided in Examples 1, 2, 3 and 4 of the present disclosure.

As show in FIG. 5, the extractive distillation system 105 comprises an extractive distillation column 201, a desulfurization column 202, a coalescence dehydrator 204 and a regeneration column 203, wherein on the top of extractive distillation column 201 is provided an inlet of extraction solvent, the feed inlet of the extractive distillation column 201 is connected with the outlet of the medium gasoline fraction through a pipeline, on the top of the extractive distillation column 201 is provided an raffinate oil outlet equipped with a reflux device, the bottom product outlet of the extractive distillation column 201 is connected with the feed inlet of the desulfurization column 202 through a pipeline, on the top of the desulfurization column 202 is provided an outlet of extracted oil before dehydration and a reflux inlet equipped with a reflux device, the coalescence dehydrator 204 is provided with an inlet of extracted oil before dehydration and an extracted oil outlet, the outlet of extracted oil before dehydration on the top of the desulfurization column 202 is connected with the reflux inlet on the top of the desulfurization column 202 and the inlet of extracted oil before dehydration of the coalescence dehydrator 204, respectively. The kettle of the desulfurization column 202 is provided with the water vapor and solvent inlet, the bottom product outlet of the desulfurization column 202 is connected with the extraction solvent inlet and the feed inlet of the regeneration column 203 through a pipeline respectively, the kettle of the regeneration column 203 is provided with the water vapor inlet, the top product outlet of the regeneration column 203 is connected with the water vapor and solvent inlet of the desulfurization column 202 through a pipeline, the regeneration column 203 is provided with a bottom deactivated solvent outlet.

As shown in FIG. 5, the medium gasoline fraction goes to the extractive distillation system 105. First, the medium gasoline fraction enters the extractive distillation column 201, and is sufficiently contacted with the extraction solvent injected from the top of the column, the extraction solvent dissolves the sulfides and aromatics in the medium gasoline fraction, which enters the bottom of the extractive distillation column 201; a raffinate oil is obtained on the top of the extractive distillation column 201, the extracted oil and solvent obtained at the bottom of the column enters the desulfurization column 202;

Then, the extracted oil and solvent are rectified in the desulfurization column 202, the water vapor and the regenerated solvent from the regeneration column are passed to the bottom of the desulfurization column 202, the top product is subjected to delamination to obtain the pre-dehydration extracted oil and water, the pre-dehydration extracted oil partially refluxed, and partially go through dehydration in the coalescence dehydrator 204 in order to obtain the extracted oil, the extracted oil is the product of this step, a portion of the solvent obtained at the bottom of the column is returned to the extractive distillation column 201 and the other portion is fed to the regeneration column 203 for solvent regeneration;

Finally, the bottom of the regeneration column 203 is introduced with the water vapor to perform stripping regeneration of solvent, the water vapor and the regenerated solvent are discharged from the top of the column, returned back to the bottom of the desulfurization column 202, and the deactivated solvent is discharged from the bottom of the column.

Wherein:

The number of column plates of the extractive distillation column 201 is 85, the number of feed plates is 52, the operating conditions are controlled to be: the column top temperature is 97° C., the column top pressure is 0.5 atm, the column kettle temperature is 165° C., the column kettle pressure is 1.35 atm, the reflux ratio is 0.5, the mass ratio of the extraction solvent and the medium gasoline fraction is 3:1.

The number of column plates of the desulfurization column 202 is 19, the number of feed plates is 3, the operating conditions are controlled to be: the column top temperature is 97° C., the column top pressure is −0.6 atm, the column kettle temperature is 174° C., the column kettle pressure is −0.4 atm, the reflux ratio is 0.5, the mass ratio of the kettle product returned to the extractive distillation column 201 and that went into the regeneration column 203 is 130:1.

The temperature of the regeneration column is controlled to be 154° C., the feed mass ratio of the water vapor and the solvent is 7:4.

The esterification reaction of raffinate oil is: Mixing the aforementioned obtained raffinate oil and the formic acid, then the mixture was contacted with the medium gasoline esterification catalyst, the olefin in the raffinate oil undergoes an esterification reaction in the medium gasoline esterification reactor 110; Mixing the reaction product with the formic acid extractant (water and formic acid aqueous solution), stirring, delaminating, to obtain the aqueous esterified medium gasoline and formic acid aqueous solution extract; the aqueous esterified medium gasoline goes through the coalescence dehydrator 111 to undergo dehydration in order to obtain the esterified medium gasoline; a portion of the formic acid aqueous solution extract are used for separation and purification of the formic acid, the other portion is further used as formic acid extractant to mix with the esterification product, stirring, delaminating, to extract the unreacted formic acid in the esterification product.

The esterification reaction conditions of the raffinate oil are: the molar ratio of the formic acid and olefins in the raffinate oil is 1:1, the reaction temperature is 120° C., the pressure is 2.0 MPa, the volume space velocity is 2.5 h$^{-1}$; in the mixture of the formic acid extractant and the esterification product, the mass ratio of the formic acid extractant and the esterification product is 1:1, the mass ratio of formic acid aqueous solution extract used for separation and purification and that used as the formic acid extractant is 1:100.

As shown in FIG. 1, the heavy gasoline fraction is mixed with the extracted oil to obtain a mixed oil, the mixed oil is subjected to the operations in series, firstly, the mixed oil is contacted with an one-stage selective hydrodesulfurization catalyst in the one-stage hydrodesulfurization reactor 106 to perform an one-stage hydrodesulfurization reaction, the reaction conditions are: the pressure is 1.5 MPa, the temperature is 250° C., the liquid volume space velocity is 3.5 h$^{-1}$, the hydrogen/oil volume ratio is 300:1; then the resultant contacts with a two-stage selective hydrodesulfurization catalyst in the two-stage hydrodesulfurization reactor 108 to perform a two-stage hydrodesulfurization reaction, the reaction conditions are: the pressure is 1.5 MPa, the temperature is 340° C., the liquid volume space velocity is 3.2 h$^{-1}$, the hydrogen/oil volume ratio is 300:1; then it enters the stripping column 108 to remove H$_2$S, the bottom temperature of the stripping column is controlled to be 175° C., the column top temperature to be 75° C., the pressure is 0.5 MPa; finally, the resultant contacts with a hydrocarbon isomerization/aromatization catalyst in the hydrocarbon isomerization/aromatization reaction 109, a hydrocarbon isomerization/aromatization reaction is performed to obtain the treated heavy gasoline, the reaction conditions are: the pressure is 1.5 MPa, the temperature is 350° C., the liquid volume space velocity is 1.5 h$^{-1}$, the hydrogen/oil volume ratio is 300:1.

After the completion of the reaction, the alkylated light gasoline, the esterified medium gasoline and the treated heavy gasoline are blended to obtain a clean gasoline product.

During the reaction, the directional sulfur transfer catalyst, the medium gasoline esterification catalyst, the one-stage selective hydrodesulfurization catalyst, the two-stage selective hydrodesulfurization catalyst and the hydrocarbon isomerization/aromatization catalyst are all diluted with porcelain sand, and after each reactor or reaction device is qualified in an air tight manner, the directional sulfur transfer catalyst, the one-stage selective hydrodesulfurization catalyst, the two-stage selective hydrodesulfurization catalyst and the hydrocarbon isomerization/aromatization catalyst were each dried and presulfurized respectively, the drying conditions are: 120° C., $N_2$ atmosphere, $N_2$ space velocity 1000 h-1; the presulfurization steps are: $N_2$ in the catalyst bed is completely replaced by $H_2$, and the space velocity of $H_2$ is maintained to be 900 h$^{-1}$, the temperature of the catalyst bed is adjusted to 150° C., a straight-run naphtha is injected to the catalyst bed at volume space velocity of 3 h$^{-1}$, the hydrogen/oil volume ratio is adjusted to 300:1; the catalyst bed is heated to 180° C. at a speed of 20° C./h, injecting of the vulcanizing agent (dimethyl disulfide) is started, with the injection rate adjusted to be 30 wt. % of straight-run naphtha, and then the temperature is raised to 230° C. at a speed of 15° C./h, and kept at this temperature for 8 h; the temperature is raised to 280° C. at a speed of 15° C./h, and kept at this temperature for 8 h; the temperature is raised to 320° C. at a speed of 15° C./h, and kept at this the temperature for 8 h; the reaction temperature of each catalyst bed is lowered at a speed of 20° C./h; Finally, the oil for the reaction is used to replace the sufurized oil in the system, the sulfidation is ended. The space velocity and hydrogen/oil ratio are adjusted, the corresponding reaction is performed according to the above steps, and the sampling analysis starts after 100 h of reaction stabilization. Table 1 shows the properties of upgraded gasoline products.

TABLE 1

The properties and parameters of the full range raw oil 1 and upgraded blended product of the light, medium and heavy gasoline in Example 1

| Item | Full range raw oil 1 | The blended product of the light, medium and heavy gasolines |
|---|---|---|
| yield (wt %) | — | 99.5 |
| density (g/mL) | 0.724 | 0.728 |
| distillation range | 34-201 | 33-202 |
| content of typical hydrocarbons (v %) | | |
| aromatics | 14.4 | 16.5 |
| olefin | 35.6 | 14.3 |
| isoparaffin | 18.2 | 25.5 |
| sulfur (μg · g$^{-1}$) | 625.3 | 8.9 |
| RON | 89.5 | 90.0 |

As can be seen from Table 1, the processing method of this Example can reduce the sulfur content of FCC gasoline from 625.3 μg·g$^{-1}$ to 8.9 μg·g$^{-1}$, and the olefin content reduces from 35.6 v % to 14.3 v %, the isoparaffin content increases from 18.2 v % to 25.5 v %, the aromatics content increases from 14.4 v % to 16.5 v %. Meanwhile the alkylation of olefins in the light gasoline fraction and esterification of olefins in the medium gasoline fraction leads to the RON of the blended product increased by 0.5 unit, the liquid yield of 99.5 wt % under the conditions of ultra-deep desulfurization and significant olefin reduction of the full range raw oil, and the blended product conforms to the requirement of National VI clean gasoline standard.

Example 2

The Example provides an efficient processing method and a system for an inferior gasoline which uses the aforementioned raw oil 1 as the raw material.

Figure 2:
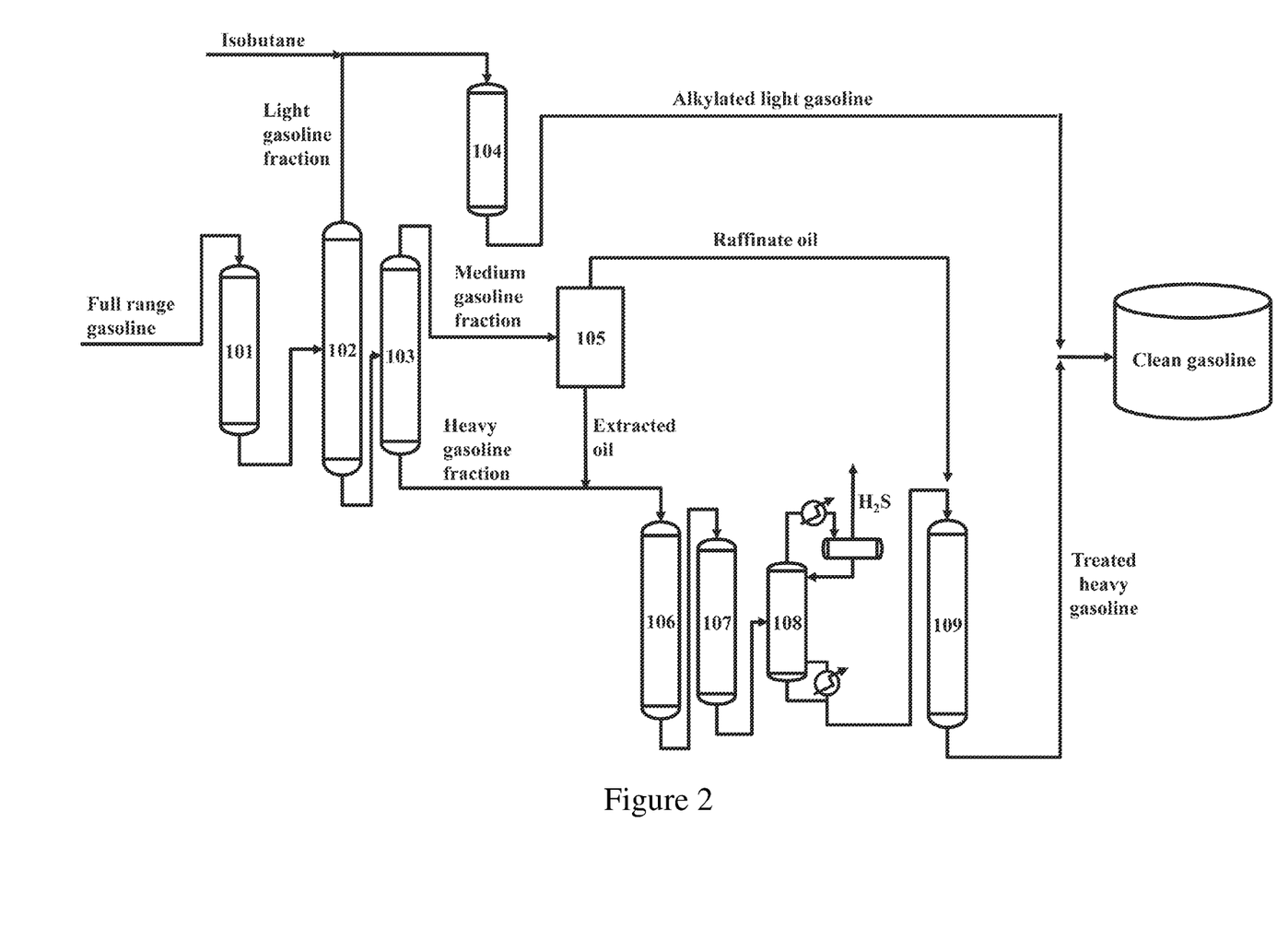
FIG. 2 is a schematic flow diagram and a system of an efficient processing method for an inferior gasoline provided in Example 2 of the present disclosure.

As shown in FIG. 2, the basic system of this Example is substantively the same as Example 1, except that the raffinate oil outlet of the extractive distillation system 105 is not connected with the inlet of raw material of reaction of the medium gasoline esterification reactor 110, but directly connected on the inlet of raw material of reaction of the hydrocarbon isomerization/aromatization reactor 109 through a pipeline. That is, the medium gasoline esterification reactor 110, the formic acid extraction system and the coalescence dehydrator 111 are not included in this system, but the raffinate oil outlet of the extractive distillation system 105 is directly connected with the inlet of raw material of reaction of the hydrocarbon isomerization/aromatization reactor 109 through a pipeline, the rest is the same as aforementioned producing system.

In accordance with the system of the Example, the process flow of the Example is similar to that of Example 1, except that the process flow of the Example does not perform the esterification reaction of the raffinate oil. Instead, the raffinate oil is mixed with the $H_2S$-removal product after the stripping column 109, together subjected to the hydrocarbon isomerization/aromatization reaction. The remaining parameters of reaction devices, the reaction conditions, the catalysts and the preparation methods and treatment thereof are all the same as Example 1, and the results are shown in Table 2:

TABLE 2

The properties and parameters of the upgraded blended product of the light, medium and heavy gasoline in Example 2

| Item | The blended product of the light, medium and heavy gasoline |
|---|---|
| yield (wt %) | 99.4 |
| density (g/mL) | 0.727 |
| distillation range | 33-203 |
| content of typical hydrocarbons (v %) | |
| aromatics | 17.9 |
| olefin | 14.5 |
| isoparaffin | 27.5 |
| sulfur (μg · g$^{-1}$) | 9.1 |
| RON | 89.8 |

As can be seen from Table 2, the modified method of this Example can reduce the sulfur content of FCC gasoline from 625.3 μg·g$^{-1}$ to 9.1 μg·g$^{-1}$, and the olefin content reduces from 35.6 v % to 14.5 v %, the isoparaffin content increases from 18.2 v % to 27.5 v %, the aromatics content increases from 14.4 v % to 17.9 v %. Meanwhile the esterification of olefins in the light gasoline fraction and the hydrocarbon isomerization/aromatization of the medium gasoline raffinate oil and the heavy gasoline fraction leads to the RON of the blended product increased by 0.3 unit, the liquid yield of 99.4 wt % under the conditions of ultra-deep desulfurization and olefin reduction of the full range raw oil, and the blended product conforms to the requirement of National VI clean gasoline standard.

Example 3

The Example provides an efficient processing method and a system for an inferior gasoline which uses a high-sulfur, high-olefin, high-benzene FCC gasoline with the sulfur content of 1230.0 $\mu g \cdot g^{-1}$, the olefin content of 42.3 v %, the aromatics content of 20.3 v %, the isoparaffin content of 20.2 v %, benzene content 1.5 v % (raw oil 2, its properties can be seen in Table 3) as the raw material.

Figure 3:
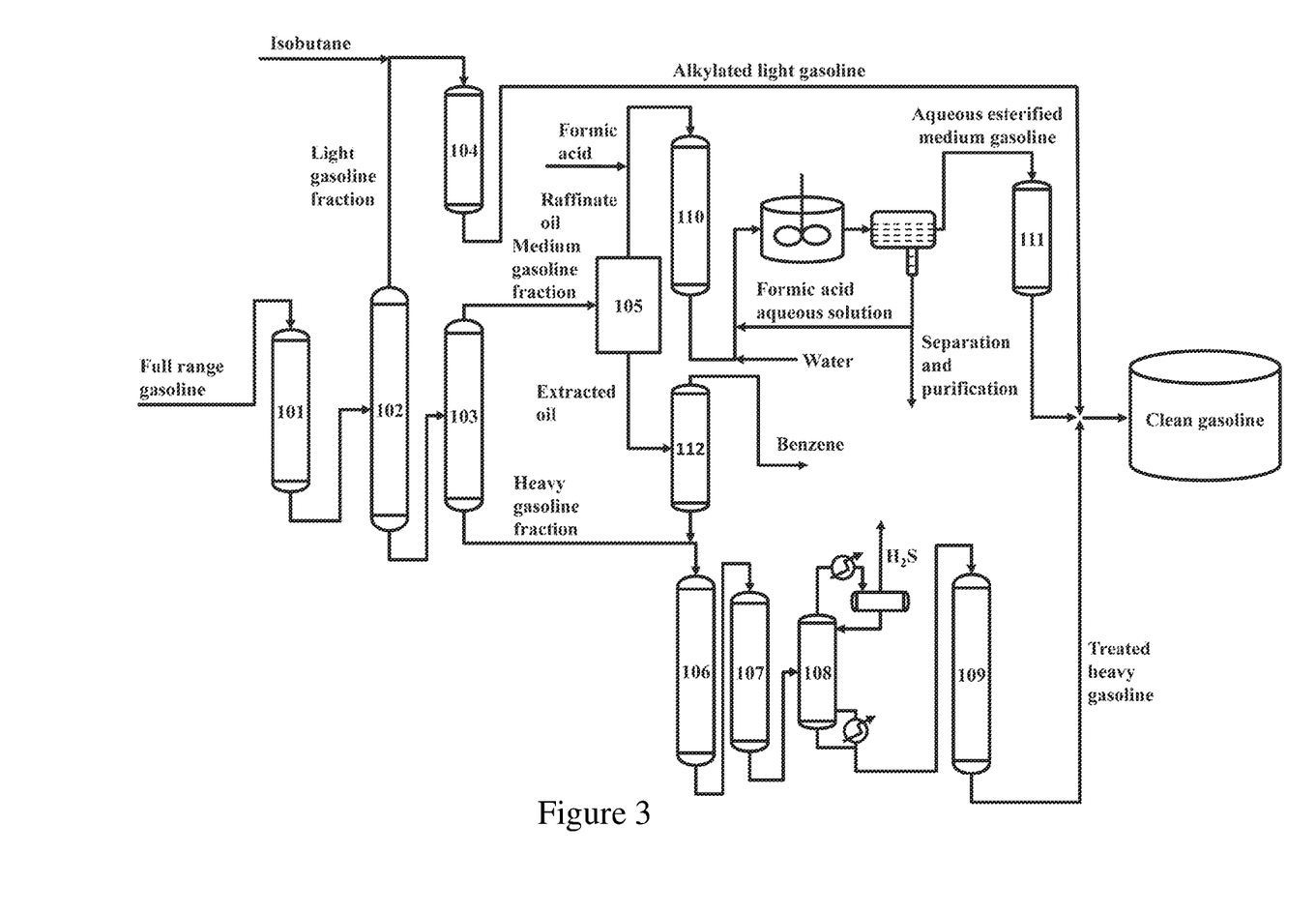
FIG. 3 is a schematic flow diagram and a system of an efficient processing method for an inferior gasoline provided in Example 3 of the present disclosure.

As shown in FIG. 3, the system of this Example is basically the same as Example 1, except that the debenzolization column 112 is provided on the pipeline between the extracted oil outlet of the extractive distillation system 105 and the reaction feed inlet of the one-stage hydrodesulfurization reactor 106, in the debenzolization column 112, the extracted oil outlet after debenzolization is connected with the one-stage hydrodesulfurization reactor 106, the rest is the same as Example 1.

The processing method of the raw oil 2 is as follows:
The system of the Example is similar to that of Example 1, in the process of the Example, the extracted oil is subjected to the debenzolization treatment before mixing with the heavy gasoline fraction, the catalysts and the preparation method thereof in the Example are the same as Example 1. Parts of the parameters of the reaction devices and the specific reaction conditions are as follows, the unmentioned parameters of the reaction devices and reaction conditions are the same as Example 1.

The reaction conditions of the directional sulfur transfer reaction are: the pressure is 2.4 MPa, the temperature is 140° C., the liquid volume space velocity is 3 $h^{-1}$, and the hydrogen/oil volume ratio is 7.

The cutting temperature of the light gasoline is 60° C., and the cutting temperature of the medium and the heavy gasoline is 140° C.; that is, the fraction which is collected below 60° C. is the light gasoline fraction, the fraction which is collected between 60° C. and 140° C. is the medium gasoline fraction, and the fraction which is collected higher than 140° C. is the heavy gasoline fraction.

The alkylation reaction conditions of the light gasoline are the same as in Example 1.

The number of column plates of the extractive distillation column 201 is 85, the number of feed plates is 52, and the operating conditions are controlled to be: the column top temperature is 92° C., the column top pressure is 0.42 atm, the column kettle temperature is 175° C., the column kettle pressure is 1.25 atm, the reflux ratio is 0.6, and the mass ratio of the extraction solvent and the medium gasoline fraction is 3.5:1.

The number of column plates of the desulfurization column 202 is 19, the number of feed plates is 3, the operating conditions are controlled to be: the column top temperature is 92° C., the column top pressure is −0.4 atm, the column kettle temperature is 175° C., the column kettle pressure is −0.4 atm, the reflux ratio is 0.6, and the mass ratio of the kettle product solvent returned to the extractive distillation column 201 and that went to the regeneration column 203 is 130:1.

The temperature of the regeneration column is controlled to be 154° C., and the mass ratio of the water vapor and the solvent is 7:4.

The esterification reaction conditions of the raffinate oil are: the pressure is 2.0 MPa, the temperature is 125° C., the liquid volume space velocity is 2.0 $h^{-1}$ (based on the formic acid), the weight ratio of the formic acid and olefins in the raffinate oil is 1.1:1, and the mass ratio of the formic acid aqueous solution extract used for separation and purification and that used as the formic acid extractant is 1:90.

The debenzolization treatment is carried out using a debenzolization column 112: the number of column plates of the debenzolization column 112 is 30, the number of feed plates is 18, and the operating conditions are controlled to be: the column top temperature is 103° C., the column top pressure is 1 atm, the column kettle temperature is 141° C., the column kettle pressure is 1.3 atm, and the reflux ratio is 2.

As shown in FIG. 3, the heavy gasoline fraction is mixed with the extracted oil which has undergone debenzolization treatment, to obtain a mixed oil. The mixed oil is subjected to the operations in series. Firstly, the mixed oil is contacted with a one-stage selective hydrodesulfurization catalyst in the one-stage hydrodesulfurization reactor 106 to perform a one-stage hydrodesulfurization reaction. The reaction conditions are: the pressure is 1.5 MPa, the temperature is 265° C., liquid volume space velocity is 3.5 $h^{-1}$, and the hydrogen/oil volume ratio is 300:1. Then it contacts with a two-stage selective hydrodesulfurization catalyst in the two-stage hydrodesulfurization reactor 107 to perform a two-stage hydrodesulfurization reaction, with the reaction conditions being: the pressure is 1.5 MPa, the temperature is 350° C., the liquid volume space velocity is 3.2 $h^{-1}$, and the hydrogen/oil volume ratio is 300:1; then it enters the stripping column 108 to remove $H_2S$, controlling the bottom temperature of the stripping column to be 175° C., with the column top temperature being 75° C., the pressure is 0.5 MPa. Finally, it contacts with a hydrocarbon isomerization/aromatization catalyst in the hydrocarbon isomerization/aromatization reaction 109, a hydrocarbon isomerization/aromatization reaction is performed, the reaction conditions being: the pressure is 1.5 MPa, the temperature is 360° C., the liquid volume space velocity is 1.5 $h^{-1}$, and the hydrogen/oil volume ratio is 300:1.

After the completion of the reaction, the alkylated light gasoline, the esterified medium gasoline and the treated heavy gasoline are blended to obtain an clean gasoline product. The properties and parameters of the gasoline are shown in Table 3.

TABLE 3

The properties and parameters of the raw oil 2 and upgraded blended product of the light, medium and heavy gasoline of Example 3

| Item | Full range raw oil 2 | The blended product of the light, medium and heavy gasoline |
|---|---|---|
| yield (wt %) | — | 99.5 |
| density (g/mL) | 0.733 | 0.731 |
| distillation range | 34-202 | 33-201 |
| content of typical hydrocarbons (v %) | | |
| aromatics | 20.3 | 23.8 |
| olefin | 42.3 | 14.9 |
| isoparaffin | 20.2 | 26.1 |

TABLE 3-continued

The properties and parameters of the raw oil 2 and upgraded blended product of the light, medium and heavy gasoline of Example 3

| Item | Full range raw oil 2 | The blended product of the light, medium and heavy gasoline |
|---|---|---|
| benzene | 1.5 | 0.7 |
| sulfur (µg · g$^{-1}$) | 1230.0 | 8.1 |
| RON | 92.1 | 92.5 |

As can be seen from Table 3, the modified method of this Example can reduce the sulfur content of FCC gasoline from 1230.0 µg·g$^{-1}$ to 8.1 µg·g$^{-1}$, the olefin content reduces from 42.3 v % to 14.9 v %, the isoparaffin content increases from 20.2 v % to 26.1 v %, the aromatics content increases from 20.3 v % to 23.8 v %, and the benzene content decreases from 1.5 v % to 0.7 v %. Meanwhile the alkylation of olefins in the light gasoline fraction and the esterification of the olefins in the medium gasoline fraction lead to the blended product RON increased by 0.4 unit under the conditions of ultra-deep desulfurization and significant olefin reduction of the raw oil 2, and the blended product conforms to the requirement of National VI clean gasoline standard.

Example 4

This Example provides an efficient processing method and a system for an inferior gasoline which uses the aforementioned raw oil 2 as the raw material.

Figure 4:
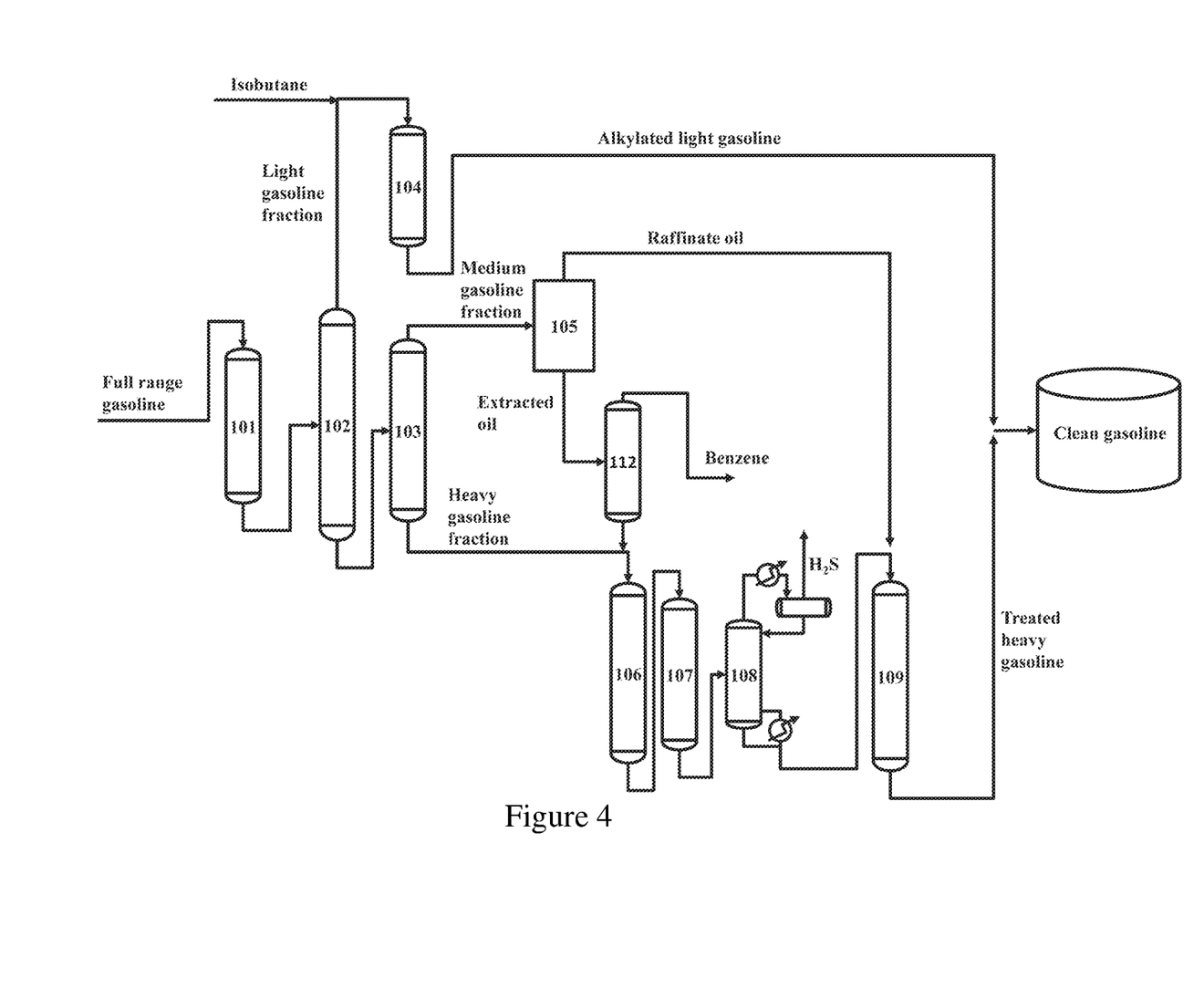
FIG. 4 is a schematic flow diagram and a system of an efficient processing method for an inferior gasoline provided in Example 4 of the present disclosure.

As shown in FIG. 4, the system of this Example is substantively the same as Example 3, except that the raffinate oil outlet of the extractive distillation system 105 is not connected with the inlet of raw material of reaction of the medium gasoline esterification reactor 110, but is directly connected on the inlet of raw material of reaction of the hydrocarbon isomerization/aromatization reactor 109 through a pipeline. That is, the medium gasoline esterification reactor 110, the formic acid extraction system and the coalescence dehydrator 111 are not provided in this Example, the raffinate oil outlet of the extractive distillation system 105 is directly connected with the inlet of raw material of reaction of the hydrocarbon isomerization/aromatization reactor 109 through a pipeline, and the rest is the same as the aforementioned system.

The system of this Example is similar to that of Example 3, except that the process of the Example does not perform the esterification reaction of the raffinate oil in Example 3. Instead, the raffinate oil is mixed with the H$_2$S-removal product following the stripping column 108, together subjected to with the hydrocarbon isomerization/aromatization reaction. The remaining preparation methods and composition of each catalyst, parameters of reaction devices, the reaction conditions are all the same as Example 3, and the properties and parameters of the obtained upgraded gasoline product are shown in Table 4.

TABLE 4

The properties and parameters of the upgraded blended product of the light, medium and heavy gasoline of Example 4

| Item | The blended product of the light, medium and heavy gasoline |
|---|---|
| yield (wt %) | 99.4 |
| density (g/mL) | 0.734 |
| distillation range | 33-203 |

TABLE 4-continued

The properties and parameters of the upgraded blended product of the light, medium and heavy gasoline of Example 4

| Item | The blended product of the light, medium and heavy gasoline |
|---|---|
| content of typical hydrocarbons (v %) | |
| aromatics | 24.8 |
| olefin | 14.2 |
| isoparaffin | 29.3 |
| benzene | 0.7 |
| sulfur (µg · g$^{-1}$) | 8.3 |
| RON | 92.1 |

As can be seen from Table 4, the modified method of this Example can reduce the sulfur content of FCC gasoline from 1230.0 µg·g$^{-1}$ to 8.3 µg·g$^{-1}$, and the olefin content reduces from 42.3 v % to 14.2 v %, the isoparaffin content increases from 20.2 v % to 29.3 v %, the aromatics content increases from 20.3 v % to 24.8 v %, and the benzene content decreases from 1.5 v % to 0.7 v %. Meanwhile the alkylation of olefins in the light gasoline fraction leads to the blended product RON without lost under the conditions of ultra-deep desulfurization, significant olefin reduction and debenzolization of the raw oil 2, and the product conforms to the requirement of National VI clean gasoline standard.

The above four Examples show that the efficient processing method and system for an inferior gasoline provided by the disclosure can upgrade the raw material gasoline with high sulfur and high olefin to the National VI clean gasoline products with sulfur content ≤10 µg·g$^{-1}$, olefin content ≤15 v %, benzene content ≤0.8 v %, and the octane value is not lost or improved in the gasoline research, indicating that the method of the disclosure has a good hydrogenation effect on inferior gasolines.

The above specific Examples further described the objects, technical solutions and advantageous effects of the present disclosure, but is not intended to limit the scope of the disclosure.

What is claimed is:

1. A method for processing an inferior gasoline, comprising the steps of:
    allowing the inferior gasoline to be contacted with a sulfur-transfer catalyst in the presence of hydrogen and undergo a sulfur transfer reaction, and then cutting the gasoline to obtain a light gasoline fraction, a medium gasoline fraction and a heavy gasoline fraction, wherein the gasoline is cut into the light gasoline fraction and the heavy component firstly, and then the heavy component is cut into a medium gasoline fraction and a heavy gasoline fraction;
    mixing the light gasoline fraction with isobutane, wherein olefins in the light gasoline fraction are subjected to an alkylation reaction under the action of a light gasoline alkylation catalyst to obtain an alkylated light gasoline;
    obtaining an olefin-rich raffinate oil and a sulfide- and aromatics-rich extracted oil by separating the medium gasoline fraction by passing the medium gasoline fraction through an extractive distillation system;
    mixing a raffinate oil with formic acid, wherein olefins in the raffinate oil are subjected to an esterification reaction under the action of a medium gasoline esterification catalyst, and then an unreacted formic acid is removed to obtain an esterified medium gasoline, or the raffinate oil is not subjected to an esterification reaction and the raffinate oil is directly mixed with product after removing the $H_2S$ to carry out a hydrocarbon isomerization/aromatization reaction;

mixing the heavy gasoline fraction with the extracted oil to obtain a mixed gasoline, wherein the mixed gasoline is successively subjected to a one-stage hydrodesulfurization reaction, a two-stage hydrodesulfurization reaction and $H_2S$-removal and a hydrocarbon isomerization/aromatization reaction to obtain a treated heavy gasoline;

wherein the one-stage hydrodesulfurization reaction occurs under the condition that the mixed gasoline is contacted with a one-stage selective hydrodesulfurization catalyst to remove macromolecular sulfides;

wherein the two-stage hydrodesulfurization reaction occurs under the condition that the product of one-stage hydrodesulfurization reaction is contacted with a two-stage selective hydrodesulfurization catalyst to remove the small molecular sulfides;

wherein the hydrocarbon isomerization/aromatization reaction occurs under the condition that the product of $H_2S$-romoval is contacted with a hydrocarbon isomerization/aromatization catalyst;

re-blending the alkylated light gasoline, the esterified medium gasoline and the treated heavy gasoline to obtain a clean gasoline, wherein the clean gasoline is a National VI clean gasoline product with sulfur content ≤10 µg·g$^{-1}$, olefin content ≤15 v %, and benzene content ≤0.8 v %.

2. The method for processing an inferior gasoline according to claim 1, wherein the extracted oil is subjected to a debenzolization treatment prior to mixing with the heavy gasoline fraction.

3. The method for processing an inferior gasoline according to claim 2, wherein the debenzolization treatment is carried out on the extracted oil using a debenzolization rectification system;

wherein the debenzolization rectification system comprises a debenzolization column, the number of column plates of the debenzolization column is 20 to 50, the number of feed plates is 10 to 40, the operating conditions are controlled to be: the column top temperature is 90 to 120° C., the column top pressure is 0.7 to 1.5 atm, the column kettle temperature is 120 to 160° C., the column kettle pressure is 1.3 to 1.7 atm, the reflux ratio is 1.5 to 2.5.

4. The method for processing an inferior gasoline according to claim 1, wherein a cutting temperature between the light gasoline fraction and the medium gasoline fraction is any point in the range of 30 to 60° C., and the cutting temperature between the medium gasoline fraction and the heavy gasoline fraction is higher than any point in the range of 60 to 1.50° C.

5. The method for processing an inferior gasoline according to claim 1, wherein the extractive distillation system comprises an extractive distillation column, a desulfurization column, an extraction oil dehydrator and a regeneration column, and wherein the step of obtaining an olefin-rich raffinate oil and a sulphide, and aromatics-rich extracted oil by separating the medium gasoline fraction by passing through the extractive distillation system comprises:

passing the medium gasoline fraction into the extractive distillation column and sufficiently contacting the medium gasoline fraction with an extraction solvent injected from a top of the extractive distillation column, wherein the raffinate oil as a top product and a mixture of extracted oil and solvents as a bottom product are obtained through rectification separation, wherein a part of the raffinate oil as the top product is reflux, wherein a part of the raffinate oil is used as a product of this step, the mixture of the extracted oil and the solvents as the bottom product being sent into the desulfurization column for rectification, wherein sufficiently contacting the medium gasoline fraction with the extraction solvent means the extraction solvent dissolves the sulfide and the aromatics in the medium gasoline;

introducing water vapor and a regenerated solvent from the regeneration column into a bottom of the desulfurization column, wherein a mixture of the extracted oil and water as a top product and the solvent as a bottom product are obtained by rectification separation, wherein the mixture of the extracted oil and water is layered to obtain a pre-dehydration extracted oil and water, a part of the pre-dehydration extracted oil being reflux, wherein a part of the pre-dehydration extracted oil is dehydrated by a extraction oil dehydrator to obtain an extracted oil and the extracted oil is the product of this step, and wherein a part of the solvent obtained at the bottom is returned to the extractive distillation column as an extraction solvent and another part of the solvent is sent into the regeneration column for solvent regeneration;

introducing a water vapor into a bottom of the regeneration column and using the water vapor to strip an entering solvent to obtain the water vapor and a regenerated solvent and a deactivated solvent, wherein the water vapor and the regenerated solvent are discharged from the top of the regeneration column and returned to the bottom of the desulfurization column, and wherein the deactivated solvent is discharged from the bottom of the regeneration column;

wherein the extraction solvent includes one or more of diethylene glycol, triethylene glycol, tetraethylene glycol, dimethyl sulfoxide, sulfolane, N-formyl morpholine, N-methyl-pyrrolidone, polyethylene glycol and propylene carbonate;

wherein the number of column plates of the extractive distillation column is 50 to 100, the number of feed plates is 30 to 70, the operating conditions are controlled to be: a range of column top temperature is 60 to 110° C., a range of column top pressure is 0.1 to 1 atm, a range of column kettle temperature is 140 to 200° C., a range of column kettle pressure is 0.5 to 1.5 atm, a range of reflux ratio is 0.1 to 3, a range of mass ratio of the extraction solvent and the medium gasoline fraction is 1 to 10:1;

wherein the extraction oil dehydrator is a coalescence dehydrator; and wherein the top temperature of the regeneration column is 100 to 200° C., the mass ratio of the introduced water vapor to the entering solvent is 0.5 to 5:1.

6. The method for processing an inferior gasoline according to claim 1, wherein the step of subjecting the olefin in the raffinate oil to an esterification reaction and then removing the unreacted formic acid to obtain an esterified medium gasoline; comprises the following steps:

mixing the raffinate oil with formic acid and adding the mixture into a medium gasoline esterification reactor, wherein by contacting with a medium gasoline esterification catalyst the olefins in the raffinate oil are esterified to obtain an esterified product;

removing the formic acid in the esterified product by an extraction operation and then dehydrating an extraction product to obtain an esterified medium gasoline;

wherein the esterified product is mixed with a formic acid extractant water and/or formic acid aqueous solution, the mixture is stirred and layered to obtain an aqueous esterified medium gasoline and a formic acid aqueous solution extract, and the aqueous esterified medium gasoline after dehydration becomes an esterified medium gasoline;

wherein the esterification reaction conditions of the raffinate oil are: a range of reaction temperatures is 80 to 200° C., a range of reaction pressures is 0.1 to 6.0 MPa, a range of weight ratios of the formic acid and the olefins in the raffinate oil is 0.5 to 2.5:1.0, and a range of liquid volume space velocities is 0.5 to 5.0 $h^{-1}$ based on the formic acid; and wherein the aqueous esterified medium gasoline is dehydrated by a coalescence dehydrator.

7. The method for processing an inferior gasoline according to claim 1, wherein the medium gasoline esterification catalyst includes one or more of a metal oxide catalyst, a zeolite molecular sieve catalyst, a $SO_4^{2-}/M_xO_y$ catalyst, a strong acid cation exchange resin catalyst or their mixture, wherein in $M_xO_y$, x is 1 to 5 and y is 1 to 8;

wherein the metal oxide catalyst comprises a catalyst made of at least one of silica, a molecular sieve and diatomite as a carrier loaded with at least one metal oxide of ZnO, SnO and $Al_2O_3$, wherein the carrier has a microporous structure or a mesoporous structure;

wherein the zeolite molecular sieve catalyst comprises a molecular sieve catalyst mixed from one or more of an aluminum phosphate molecular sieve, a silicoaluminophosphate molecular sieve, a H-type mordenite, a HY zeolite, a H-β zeolite, a HZSM-5 zeolite and a silicon-containing alumina, and wherein the zeolite molecular sieve is a micropore zeolite molecular sieve or a cascade pore zeolite molecular sieve;

wherein the $SO_4^{2-}/M_xO_y$ catalyst includes a $SO_4^{2-}/M_xO_y$ catalyst prepared by loading $SO_4^{2-}$ onto a carrier made of at least one metal oxide of ZrO, ZnO and SnO;

wherein the strong acid cation exchange resin catalyst includes a mesoporous-macroporous cross-linked polymer catalyst comprising a strong acid reactive group.

8. The method for processing an inferior gasoline according to claim 6, wherein the medium gasoline esterification catalyst includes one or more of a metal oxide catalyst, a zeolite molecular sieve catalyst, a $SO_4^{2-}/M_xO_y$ catalyst, a strong acid cation exchange resin catalyst or a mixture thereof, wherein in $M_xO_y$, x is 1 to 5 and y is 1 to 8;

wherein the metal oxide catalyst comprises a catalyst made of at least one of silica, a molecular sieve and diatomite as a carrier loaded with at least one metal oxide of ZnO, SnO and $Al_2O_3$, wherein the carrier has a microporous structure or a mesoporous structure;

wherein the zeolite molecular sieve catalyst comprises a molecular sieve catalyst mixed from one or more of an aluminum phosphate molecular sieve, a silicoaluminophosphate molecular sieve, a H-type mordenite, a HY zeolite, a H-β zeolite, a HZSM-5 zeolite and a silicon-containing alumina, and the zeolite molecular sieve is a micropore zeolite molecular sieve or a cascade pore zeolite molecular sieve;

wherein the $SO_4^{2-}/M_xO_y$ catalyst includes a $SO_4^{2-}/M_xO_y$ catalyst prepared by loading $SO_4^{2-}$ onto a carrier made of at least one metal oxide of ZrO, ZnO and SnO;

wherein the strong acid cation exchange resin catalyst includes a mesoporous-macroporous cross-linked polymer catalyst comprising a strong acid reactive group.

9. The method for processing an inferior gasoline according to claim 1, wherein the two-stage selective hydrodesulfurization catalyst comprises: $MoO_3$ 3 to 10 wt. %, NiO 5 to 20 wt. %, $K_2O$ 1 to 7 wt. % and the balance being Al—Si composite oxide carrier, based on 100% of the total weight of the two-stage selective hydrodesulfurization catalyst, and the weight composition of the Al—Si composite oxide in the catalyst is: $Al_2O_3$ 60 to 75 wt. %, $SiO_2$ 5 to 15 wt. %.

10. The method for processing an inferior gasoline according to claim 7, wherein the strong acid reactive group is sulfonic acid group-$SO_3H$.

11. The method for processing an inferior gasoline according to claim 8, wherein the strong acid reactive group is sulfonic acid group-$SO_3H$.

12. The method for processing an inferior gasoline according to claim 1, wherein the inferior gasoline is a full range FCC gasoline having a sulfur content of 300 to 2000 $\mu g \cdot g^{-1}$, and an olefin content of 25 to 50 v %.

13. The method for processing an inferior gasoline according to claim 12, wherein the inferior gasoline is a full range FCC gasoline having the sulfur content of 500 to 2000 $\mu g \cdot g^{-1}$.

14. The method for processing an inferior gasoline according to claim 12, wherein the inferior gasoline is a full range FCC gasoline having the olefin content of 30 to 50 v %.

15. The method for processing an inferior gasoline according to claim 5, wherein the number of column plates of the desulfurization column is 15 to 35, the number of feed plates is 1 to 20, the operating conditions are controlled to be: the range of column top temperature is 40 to 80° C., the range of column top pressure is −1 to 0 atm, the range of column kettle temperature is 1.40 to 200° C., the range of column kettle pressure is −1 to 0 atm, the range of reflux ratio is 0.1 to 3.

16. The method for processing an inferior gasoline according to claim 1, wherein the sulfur-transfer catalyst comprises one or more transition metal oxides and a zeolite.

* * * * *